United States Patent
Josten et al.

(10) Patent No.: US 8,911,019 B2
(45) Date of Patent: Dec. 16, 2014

(54) ADJUSTABLE AND RECONFIGURABLE HEAD ARRAY SYSTEM FOR A POWER WHEELCHAIR

(75) Inventors: Johannes Engelmundus Leonardus Mathias Josten, Eindhoven (NL); Jeremy Michael Sedlak, Nashville, TN (US); Hymie Pogir, Austin, TX (US); Hans Leon Fraeyman, Eeklo (BE)

(73) Assignee: Permobil AB, Timra (SE)

( * ) Notice: Subject to any disclaimer, the term of this patent is extended or adjusted under 35 U.S.C. 154(b) by 284 days.

(21) Appl. No.: 13/412,273

(22) Filed: Mar. 5, 2012

(65) Prior Publication Data

US 2013/0228030 A1    Sep. 5, 2013

(51) Int. Cl.
*A47C 7/36* (2006.01)

(52) U.S. Cl.
USPC .......................... 297/405; 297/217.3; 297/391

(58) Field of Classification Search
USPC ....................................... 297/217.3, 391, 405
See application file for complete search history.

(56) References Cited

U.S. PATENT DOCUMENTS

| | | | | |
|---|---|---|---|---|
| 3,761,126 | A * | 9/1973 | Mulholland | 297/467 |
| 4,114,946 | A * | 9/1978 | Hoffmeister et al. | 297/217.3 |
| 4,266,825 | A * | 5/1981 | Le Donne | 297/188.18 |
| 4,732,423 | A | 3/1988 | Condon | |
| 5,791,735 | A * | 8/1998 | Helman | 297/407 |
| 5,803,642 | A * | 9/1998 | Sassmannshausen | 403/90 |
| 5,967,613 | A * | 10/1999 | McKeever | 297/397 |
| 6,419,321 | B1 * | 7/2002 | Sack | 297/405 |
| 2003/0205420 | A1 * | 11/2003 | Mulhern et al. | 180/65.1 |
| 2005/0183900 | A1 * | 8/2005 | Goertzen et al. | 180/311 |
| 2008/0302938 | A1 * | 12/2008 | Goodwin et al. | 248/288.51 |

OTHER PUBLICATIONS

EN 12184:2009 published Mar. 2010.*
ISO 7176-21:2003 published Mar. 2010.*
PCT Notification of Transmittal of the International Search Report and the Written Opinion of the International Search Authority, or the Declaration, Jun. 28, 2012, 13 pages.

* cited by examiner

*Primary Examiner* — Philip Gabler
(74) *Attorney, Agent, or Firm* — McAndrews, Held & Malloy, Ltd.

(57) ABSTRACT

Certain embodiments provide a head array system for a power wheelchair, including a head array body and one or more lateral arms. The head array body includes shafts. Each of the shafts includes lateral arm receiving sections. The one or more lateral arms are detachably coupled to one of the lateral arm receiving sections of one of the shafts.

22 Claims, 7 Drawing Sheets

ADJUSTABLE AND RECONFIGURABLE HEAD ARRAY SYSTEM FOR A POWER WHEELCHAIR

CROSS-REFERENCE TO RELATED APPLICATIONS/INCORPORATION BY REFERENCE

[Not Applicable]

FEDERALLY SPONSORED RESEARCH OR DEVELOPMENT

[Not Applicable]

MICROFICHE/COPYRIGHT REFERENCE

[Not Applicable]

FIELD OF THE INVENTION

Certain embodiments of the invention relate to a reconfigurable and adjustable head array system for use with power wheelchairs.

BACKGROUND OF THE INVENTION

Head array devices allow a user of a power wheelchair to control various functions (also referred to as modes) of the wheelchair and other connected components. For example, a head array may allow a user to activate switches or sensors using the user's head to drive the wheelchair, elevate, tilt and/or recline the wheelchair seat, and control the wheelchair leg rests. Further, a head array can allow a user to activate switches or sensors using the user's head to interact with a computer by moving a mouse, for example. As another example, a head array may allow a user to activate switches or sensors using the user's head to open doors and interact with patient rehabilitation equipment, among other things. Additionally, a head array can allow a user to perform an emergency stop of the power wheelchair, for example.

Existing head array devices typically include one to three main switches or sensors in a headrest. A first switch or sensor is typically integrated into a rear headrest of the head array, which is commonly referred to as an occipital pad. The occipital pad can be mounted to a head array base structure that is mounted to the power wheelchair. Optional second and third switches or sensors may be integrated into headrest wings that extend on one or both sides of a user's head. Alternatively, the optional second and third switches or sensors can be integrated into pads that are held in place on one or both sides of a user's head using head array lateral arms that attach to the head array base structure. In some current head array devices, an additional mode switch or sensor may also be held in place on one side of a user's head using an additional head array lateral arm that attaches to the head array base structure.

As an example, to drive a power wheelchair using a head array device having three primary sensors and the mode switch, the first sensor integrated into the rear of the headrest can allow the user to drive straight forward or straight backward depending on the selected mode. The second sensor on the left side of the user's head and a third sensor on the right side of the user's head may allow a user to turn left and right, respectively. The mode switch can allow a user to switch between driving forward and driving backward. Additionally, the mode switch may allow a user to switch to other modes, such as performing an emergency stop, adjusting the wheelchair seat or leg rests, controlling a computer mouse, opening doors, and interacting with patient rehabilitation equipment, for example.

Current head array devices suffer from several limitations. For example, in many current head array devices, the length of the lateral arms may not be adjustable. Instead, the lateral arms once positioned for a particular user are cut to a specific length. Other existing head array devices may include adjustable lateral arms where the unused sections of the lateral arms extend behind the headrest. In addition to having a bulky and disorganized appearance, the unused lateral arm section may present a hazard in that other objects in the user's environment may hook, snag or otherwise make contact with the unused lateral arm sections extending behind the headrest.

As another example, existing head array devices cannot change the configuration of the lateral sensor arms in relation to each other and to a mode switch arm. A clinician, technician or caregiver fitting the head array for the user cannot move a right lateral sensor arm to the left side. Further, if a mode switch is attached to the head array base structure below a right lateral arm, a clinician, technician or caregiver cannot remove the mode switch arm and right lateral sensor arm and reattach the mode switch arm above the right lateral arm. Instead, current head array devices are typically custom ordered and are not capable of alteration. As such, a new head array would need to be ordered if a different configuration was needed for or desired by a user. Additionally, because the lateral arms of existing head array devices are not easily removable, the existing head array devices are more difficult to clean.

Further, head array devices are exempt from various regulations such as, for example, electromagnetic compatibility (EMC), electromagnetic interference (EMI), and electrostatic discharge (ESD) standards because head arrays are considered an aftermarket accessory. Current head array devices do not meet the regulations set forth in EMC, EMI and ESD, among others. Although head array devices are exempt from complying with those and other standards, compliance with the standards results in safer head array devices.

Also, as discussed above, existing head array devices may include a single sensor in the occipital pad of the head array. However, perspiration, hair product or other moisture may soak the occipital pad, creating a conductive mass that causes unintentional activation of the sensor. Unintentional activation of the occipital pad sensor may be frustrating and hazardous for a user.

Additionally, existing head array devices are bulky and have disorganized cable management with multiple cable connections at different points on or around the power wheelchair. For example, cables can be untidily attached to an outer surface of the lateral arms. As another example, cables from different switches or sensors of existing head array devices may be routed to separate control boxes located at various locations on or around the power wheelchair.

As such, there is a need for providing uncomplicated position adjustability for head array lateral arms. Further, there is a need for a head array device that allows the addition of sensors, the removal of sensors, and the reconfiguration of the locations of existing sensors. Also, there is a need for a head array that complies with EMC, EMI and ESD regulations. Additionally, there is a need for a safeguard to prevent unintentional activation of the occipital pad sensor. Further, there is a need for cleanly managing head array cables and for providing a central connection location for the head array cables.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

An adjustable and reconfigurable power wheelchair head array system is provided, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

Figure 1:
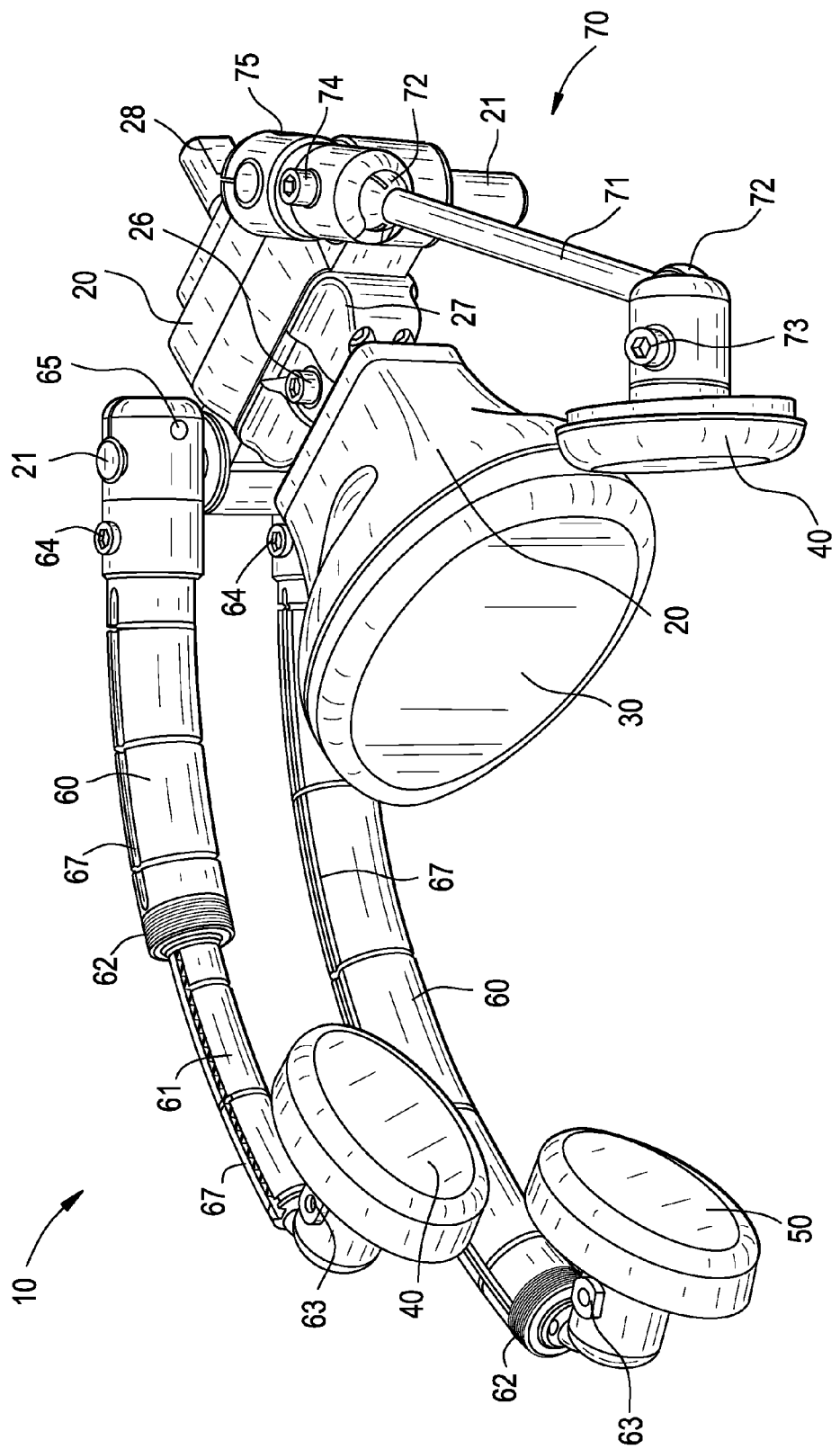
FIG. 1 is a diagram that illustrates a perspective view of an exemplary head array system in accordance with an embodiment of the present invention.

The foregoing summary, as well as the following detailed description of certain embodiments of the present invention, may be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION

Certain embodiments of the invention may be found in an adjustable and reconfigurable power wheelchair head array system comprising a head array body 20 and one or more lateral arms 60, 70. The head array body 20 comprises shafts 21. Each of the shafts 21 comprises lateral arm receiving sections. The one or more lateral arms 60, 70 are detachably coupled to one of the lateral arm receiving sections of one of the shafts 21.

Certain embodiments provide a head array system 10 for a power wheelchair, comprising a head array body 20, one or more of a sensor 40, 50 and a switch 40, 50, and one or more lateral arms 60 operable to couple the one or more of the sensor 40, 50 and the switch 40, 50 to the head array body 20. The one or more lateral arms 60 comprise a hollow, curved lateral arm tube 60 attached to the head array body 20, a curved telescoping extension 61 attached to the one or more of the sensor 40, 50 and the switch 40, 50, and a first securing mechanism 62. The telescoping extension 61 is slidable from a selectable non-extended position, where the telescoping extension 61 is substantially housed within the lateral tube 60, to selectable extension positions at least partially outside of the lateral arm tube 60. The first securing mechanism 62 is operable to lock the telescoping extension 61 into one or more of the selectable non-extended positions and the selectable extension positions.

Certain embodiments provide a head array system 10 for a power wheelchair, comprising a head array body 20 and an occipital pad. The head array body 20 comprises a microprocessor configured to generate command signals in response to sensor activation signals. The occipital pad is attached to the head array body 20 and comprises a plurality of sensors 30. Each of the plurality of sensors 30 is configured to transmit an activation signal to the microprocessor in response to sensor activation. The microprocessor generates a command signal if the microprocessor receives the activation signal from all of the plurality of sensors 30 in the occipital pad, and disregards the activation signal if the microprocessor receives the activation signal from less than all of the plurality of sensors 30 in the occipital pad.

FIG. 1 is a diagram that illustrates a perspective view of an exemplary head array system 10 in accordance with an embodiment of the present invention. Referring to FIG. 1, there is shown a head array system 10. The head array system 10 may comprise one or more of occipital pad sensors or switches 30, lateral sensors or switches 40, and mode sensors or switches 50. Switches may be activated by applying a physical force to depress the switch, for example. Sensors may be activated by detecting an object within proximity of the sensor, for example. As an example, if a user's head is detected within certain proximity of a sensor (e.g., approximately 0.25 inches or 6 millimeters, among other things), the sensor may be activated. Although certain embodiments may refer to sensors, for example, unless so claimed, the scope of various aspects of the present invention should not be limited to sensors and may additionally and/or alternatively include switches as well, or vice versa.

Referring again to FIG. 1, occipital pad sensor(s) 30 are attached to head array body 20. In various embodiments, occipital pad sensor(s) 30 include two sensors in one or more occipital pads. Occipital pad sensors 30 may be configured such that, when both occipital pad sensors 30 are activated, a microprocessor (not shown) in head array body 20 receives the activation signals from the sensors 30 and generates a command signal corresponding to the activation of the sensors 30. In certain embodiments, if the microprocessor only receives an activation signal from one of the two sensors 30, the microprocessor does not generate a command signal. For example, if perspiration, hair product or some other form of moisture saturates a portion of the headrest pad protecting the occipital pad sensors 30, the moisture may create a conductive mass that causes an unintentional activation of one of the sensors 30. An occipital pad sensor 30 configuration where two sensor activation signals are used to generate a command signal at the microprocessor may reduce or prevent unintentional command signals to be generated at the microprocessor. In various embodiments, the microprocessor generates command signals in response to receiving activation signals from one or both of the occipital pad sensors 30. Although the above description of the occipital pad sensors 30 relates to configurations for two sensors, the use of more or less sensors is also contemplated. For example, occipital pad sensors 30 may comprise one or three sensors, among other things. Further, certain embodiments may omit the occipital pad sensors 30.

Certain embodiments provide one or more lateral sensors 40 that are attached to head array body 20 via lateral arms 60, 70. FIGS. 1-7 illustrate two exemplary lateral arm embodiments, a telescoping lateral arm embodiment 60 and a swivel lateral arm embodiment 70 as discussed in more detail below. Although lateral sensors 40 are illustrated as attaching to head array body 20 using different lateral arm embodiments 60, 70, the various embodiments may use the same lateral arm embodiment or any combination of lateral arm embodiments. Further, although two lateral sensors 40 are illustrated in FIGS. 1-7, the use of more or less lateral sensors is also contemplated. For example, one or three lateral sensors 40 may be used and may be attached at either side of head array body 20 using lateral arms 60, 70. Also, certain embodiments may omit the lateral sensors 40 and lateral arms 60, 70.

In response to activation of a lateral sensor or switch 40, an activation signal is sent via a cable, for example, that runs from the lateral sensor 40 to a microprocessor that may be housed in head array body 20. The cable may be secured by one or more o-rings, or any other suitable securing mechanism(s), in a channel or groove 67 in lateral arm 60, 70 and/or lateral arm telescoping extension 61 to manage the cable and present a clean finish. In response to receiving an activation signal from lateral sensor 40, the microprocessor generates a command signal corresponding to the activation of the sensor 40. For example, if a selected head array mode is a power wheelchair forward drive mode, activation of a lateral sensor 40 on a user's left results in an activation signal being sent to the microprocessor, which generates a command signal that may command the power wheelchair to turn left, depending on the configuration of the sensors 30, 40, 50. Additionally and/or alternatively, the command signal generated by the microprocessor may be provided to primary electronics (e.g., the power module) of the power wheelchair.

In various embodiments, one or more mode, switches 50 may be attached to one or both sides of head array body 20 via lateral arms 60, 70. Although one mode switch 50 is illustrated in FIGS. 1-7, the use of more or less mode switches is contemplated. For example, two mode switches 50 may be used and may be attached at one or both sides of head array body 20 using lateral arms 60, 70. Also, certain embodiments may omit the mode switch 50 and corresponding lateral arm 60, 70. In response to activation of mode switch 50, an activation signal is sent via a cable, for example, that runs from the mode switch 50 to a microprocessor that may be housed in head array body 20. The cable may be secured by one or more o-rings, or any other suitable securing mechanism(s), in a channel or groove 67 in lateral arm 60, 70 and/or lateral arm telescoping extension 61 to manage the cable and present a clean finish.

In various embodiments, in response to receiving an activation signal from mode switch 50, the microprocessor may generate a command signal corresponding to the activation of the mode switch 50 and output the command signal to primary electronics (e.g., the power module) of the power wheelchair. The command signal may be used by the primary electronics to alter the operating mode of the head array 10. For example, activation of mode switch 50 by a user results in an activation signal being sent to the microprocessor, which generates a command signal sent to primary electronics of the power wheelchair that may change the head array 10 operating mode from a power wheelchair forward drive mode to a power wheelchair reverse drive mode, among other things. As another example, activation of mode switch 50 by a user results in an activation signal being sent to the microprocessor, which generates a command signal sent to primary electronics of the power wheelchair that may change the head array 10 operating mode from a power wheelchair drive mode to a power wheelchair seat adjustment mode, among other things.

In certain embodiments, in response to receiving an activation signal from mode switch 50, the microprocessor may update an operating mode state in the corresponding microprocessor memory in response to receiving an activation signal from mode switch 50. For example, activation of mode switch 50 by a user results in an activation signal being sent to the microprocessor, which updates an operating mode state within the microprocessor memory that may change the head array 10 operating mode from a power wheelchair forward drive mode to a power wheelchair reverse drive mode, among other things. As another example, activation of mode switch 50 by a user results in an activation signal being sent to the microprocessor, which updates an operating mode state within the microprocessor memory that may change the head array 10 operating mode from a power wheelchair drive mode to a power wheelchair seat adjustment mode, among other things.

Certain embodiments provide telescoping lateral arm 60 for coupling sensor 40, 50 to head array body 20. Telescoping lateral arm 60 is adjustable such that a position of sensor 40, 50 may be set and/or changed based on user, clinician, technician or caregiver preferences, for example. Telescoping lateral arm 60 may be a rigid, curved, hollow tube comprising a telescoping extension 61, securing mechanisms 62-65 and/or rotational mechanisms 66, for example. Telescoping extension 61 may be a rigid, curved tube that is housed substantially within telescoping lateral arm 60 when in a non-extended position and may extend at least in part from telescoping lateral arm 60 at varying extension lengths, for example.

Securing mechanism 62 may lock telescoping extension 61 at a clinician, technician or caregiver selectable length. For example, securing mechanism 62 may lock telescoping extension 61 in a non-extended position or at any suitable extension point when in an extended position. As such, the position of the sensor 40, 50 may be adjustable in a horizontal plane extending in a direction substantially from a rear of the head array 10 to the front of the head array 10. Securing mechanism 62 may be a locking ring, clamp, bolt or any other suitable securing mechanism. In various embodiments, the securing mechanism 62 may be a toolless securing mechanism.

Securing mechanism 63 may secure sensor 40, 50 to telescoping extension 61 at rotational mechanism 66, for example. Sensor 40, 50 may be removed for cleaning or replacement, among other things, by removing or unlocking, for example, securing mechanism 63. Additionally and/or alternatively, loosening or unlocking, for example, securing mechanism 63 may allow for rotation of sensor 40, 50 around rotational mechanism 66 such that the angle that sensor 40, 50 is presented toward a user's head is adjustable. Sensor 40, 50 may be fixably secured at a selected angle by tightening or locking, for example, securing mechanism 63. In certain embodiments, securing mechanism 63 may be a clamp, bolt or any other suitable securing mechanism. In various embodiments, the securing mechanism 63 may be a toolless securing mechanism. Rotational mechanism 66 may be a ball joint or any other suitable rotational mechanism, for example.

In various embodiments, securing mechanism 64 secures telescoping lateral arm 60 at a desired rotation allowing sensor 40, 50 to be adjustable in a vertical plane. For example, sensor 40, 50 may be adjusted higher or lower by rotating the curved telescoping lateral arm 60 when the securing mechanism 64 is unlocked, loosened, or the like. Once the curved telescoping lateral arm 60 is rotated such that sensor 40, 50 is at a desired height, securing mechanism 64 may be tightened or locked, for example, such that the curved telescoping lateral arm 60 is fixably secured at the selected rotation. Securing mechanism 64 may be a clamp, bolt or any other suitable securing mechanism. In various embodiments, the securing mechanism 64 may be a toolless securing mechanism.

In certain embodiments, securing mechanism 65 may secure telescoping lateral arm 60 to head array body 20 at head array shaft 21, for example. Telescoping lateral arm 60 may be removed for cleaning, replacement, and/or reconfiguration of lateral arm 60 placement, among other things, by removing or unlocking, for example, securing mechanism 65. For example, a clinician, technician or caregiver may switch positions of sensor 40 and mode switch 50 by removing each of the lateral arms 60 and reattaching the lateral arms 60 at exchanged positions on head array shaft 21. Additionally and/or alternatively, loosening or unlocking, for example, securing mechanism 65 may allow for rotation of lateral arm 60 in a horizontal plane around head array shaft 21 such that the distance between sensor 40, 50 and a user's head is adjustable. Lateral arm 60 may be fixably secured at a selected position by tightening or locking, for example, securing mechanism 65. In certain embodiments, securing mechanism 65 may be a clamp, bolt or any other suitable securing mechanism. In various embodiments, the securing mechanism 65 may be a toolless securing mechanism.

Certain embodiments provide swiveling lateral arm 70 for coupling sensor 40, 50 to head array body 20. Swiveling lateral arm 70 is adjustable such that a position of sensor 40, 50 may be set and/or changed based on user, clinician, technician or caregiver preferences, for example. Swiveling lateral arm 70 may comprise a rod 71, securing mechanisms 73-75 and/or rotational mechanisms 72, for example. Rod 71 may be a rigid tube, for example. In certain embodiments, rod 71 may be hollow such that a cable running from sensor 40, 50 to the microprocessor in head array body 20 may be enclosed in hollow rod 71 to manage the cable and present a clean finish. In various embodiments, rod 71 may be a solid rod 71 such that a cable running from sensor 40, 50 to the microprocessor in head array body 20 may be detachably coupled to an outer surface of rod 71. In an embodiment, rod 71 may comprise a groove or channel such that the cable may be secured by one or more o-rings, or any other suitable securing mechanism(s), in the groove or channel of rod 71 to manage the cable and present a clean finish.

Securing mechanism 73 may secure sensor 40, 50 to one end of rod 71 at rotational mechanism 72, for example. Sensor 40, 50 may be removed for cleaning or replacement, among other things, by removing or unlocking, for example, securing mechanism 73. Additionally and/or alternatively, loosening or unlocking, for example, securing mechanism 73 may allow for rotation of sensor 40, 50 around rotational mechanism 72 such that the angle that sensor 40, 50 is presented toward a user's head is adjustable. Sensor 40, 50 may be fixably secured at a selected angle by tightening or locking, for example, securing mechanism 73. In certain embodiments, securing mechanism 73 may be a clamp, bolt or any other suitable securing mechanism. In various embodiments, the securing mechanism 73 may be a toolless securing mechanism. Rotational mechanism 72 may be a ball joint or any other suitable rotational mechanism, for example.

In various embodiments, securing mechanism 74 secures rod 71 at a desired rotation using rotational mechanism 72 to allow sensor 40, 50 to be adjustable in vertical and horizontal planes. For example, sensor 40, 50 may be adjusted higher or lower and nearer or farther from a user's head by rotating the rod 71 at rotational mechanism 72 when the securing mechanism 74 is unlocked, loosened, or the like. Once the rod 71 is rotated such that sensor 40, 50 is at a desired height and distance from a user's head, securing mechanism 74 may be tightened or locked, for example, such that the rod 71 is fixably secured at the selected rotation. Securing mechanism 74 may be a clamp, bolt or any other suitable securing mechanism. In various embodiments, the securing mechanism 74 may be a toolless securing mechanism. Rotational mechanism 72 may be a ball joint or any other suitable rotational mechanism, for example.

In certain embodiments, securing mechanism 75 may secure swiveling lateral arm 70 to head array body 20 at head array shaft 21, for example. Swiveling lateral arm 70 may be removed for cleaning, replacement, and/or reconfiguration of lateral arm 70 placement, among other things, by removing or unlocking, for example, securing mechanism 75. For example, a clinician, technician or caregiver may switch positions of sensor 40 and mode switch 50 by removing each of the lateral arms 60, 70 and reattaching the lateral arms 60, 70 at exchanged positions on head array shafts 21. Additionally and/or alternatively, loosening or unlocking, for example, securing mechanism 75 may allow for rotation of lateral arm 70 in a horizontal plane around head array shaft 21 such that the distance between sensor 40, 50 and a user's head is further adjustable. Lateral arm 70 may be fixably secured at a selected position by tightening, or locking, for example, securing mechanism 75. In certain embodiments, securing mechanism 75 may be a clamp, bolt or any other suitable securing mechanism. In various embodiments, the securing mechanism 75 may be a toolless securing mechanism.

Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example, which are discussed in more detail below with regard to FIG. 4.

Figure 2:
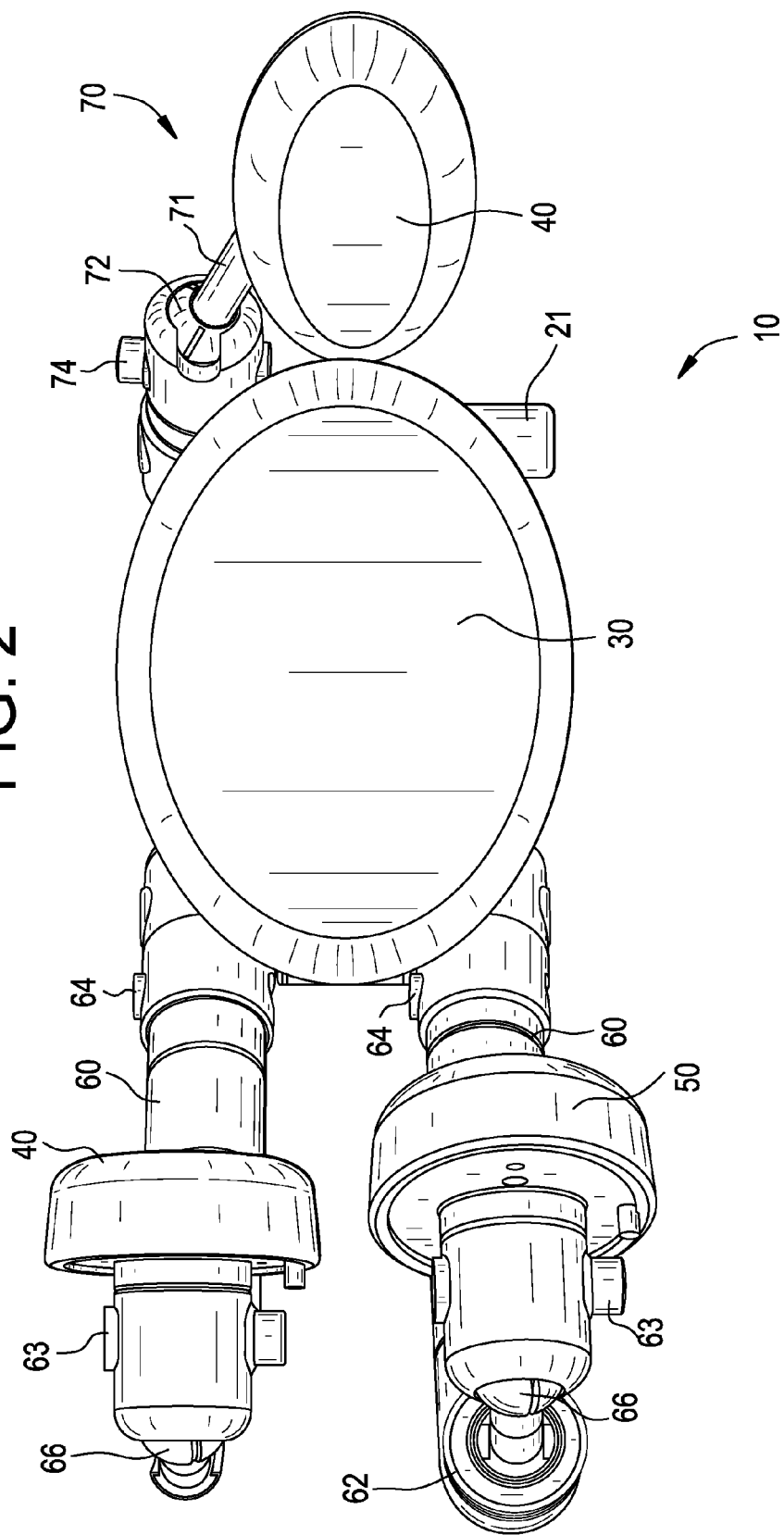
FIG. 2 is a diagram that illustrates a front view of an exemplary head array system in accordance with an embodiment of the present invention.

FIG. 2 is a diagram that illustrates a front view of an exemplary head array system 10 in accordance with an embodiment of the present invention. Referring to FIG. 2, there is shown a head array 10 comprising occipital pad sensor 30, lateral sensors 40 and mode switch 50. Occipital pad sensor 30 is attached to head array body 20 as illustrated in FIGS. 1, 3 and 5-7. Lateral arms 60, 70 couple sensors 40, 50 to head array body 20 at shafts 21. Telescoping lateral arm 60 may comprise a telescoping extension 61, securing mechanisms 62-65 and/or rotational mechanisms 66, for example. Swiveling lateral arm 70 may comprise a rod 71, securing mechanisms 73-75 and/or rotational mechanisms 72, for example. The head array 10 illustrated in FIG. 2 shares various characteristics with the head array 10 illustrated in FIG. 1 as described above.

Figure 3:
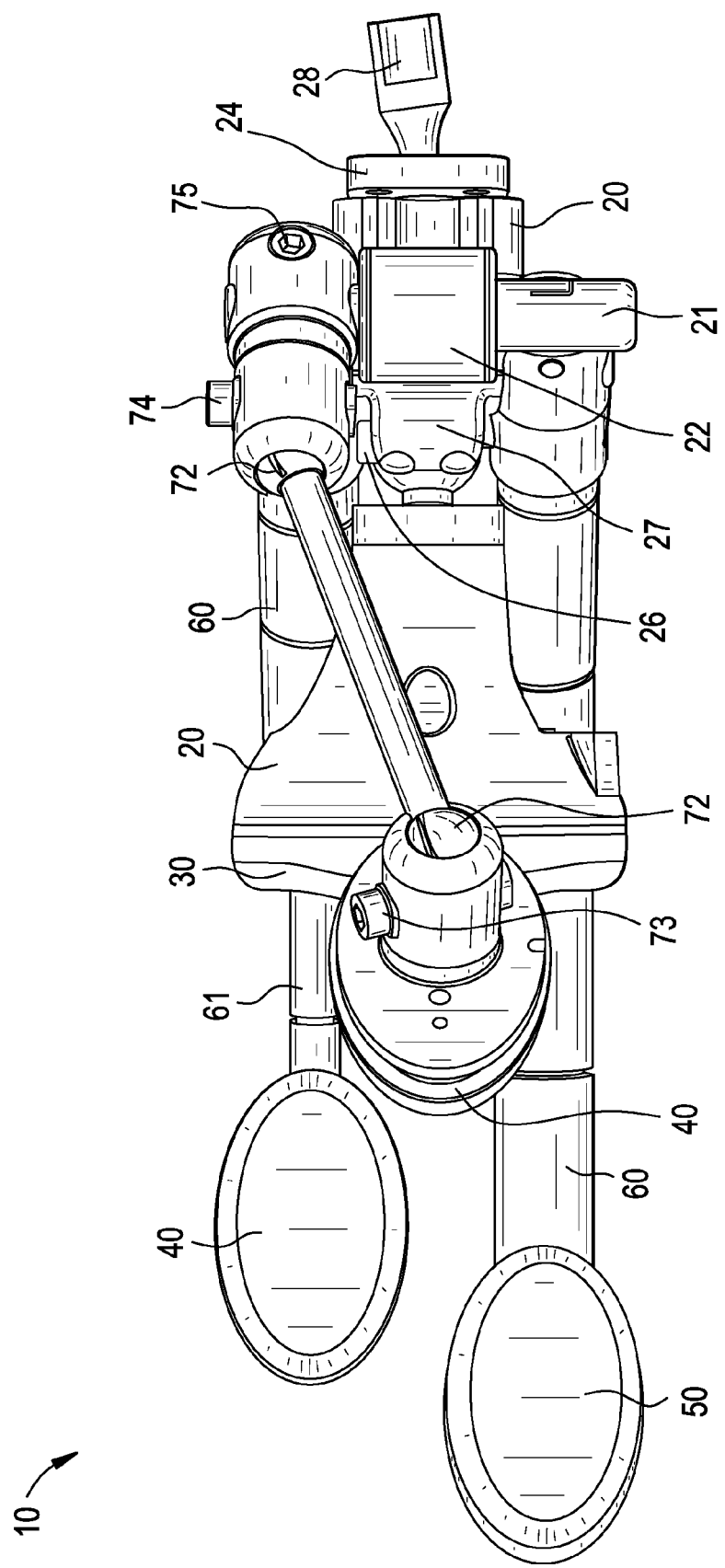
FIG. 3 is a diagram that illustrates a side view of an exemplary head array system in accordance with an embodiment of the present invention.

FIG. 3 is a diagram that illustrates a side view of an exemplary head array system 10 in accordance with an embodiment of the present invention. Referring to FIG. 3, there is shown a head array 10 comprising head array body 20, occipital pad sensor 30, lateral sensors 40 and mode switch 50. Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example. Occipital pad sensor 30 is attached to head array body 20. Lateral arms 60, 70 couple sensors 40, 50 to head array body 20 at shafts 21.

Telescoping lateral arm 60 may comprise a telescoping extension 61, securing mechanisms 62-65 and/or rotational mechanisms 66, for example. Swiveling lateral arm 70 may comprise a rod 71, securing mechanisms 73-75 and/or rotational mechanisms 72, for example. The head array 10 illustrated in FIG. 3 shares various characteristics with the head array 10 illustrated in FIGS. 1-2 as described above.

Figure 4:
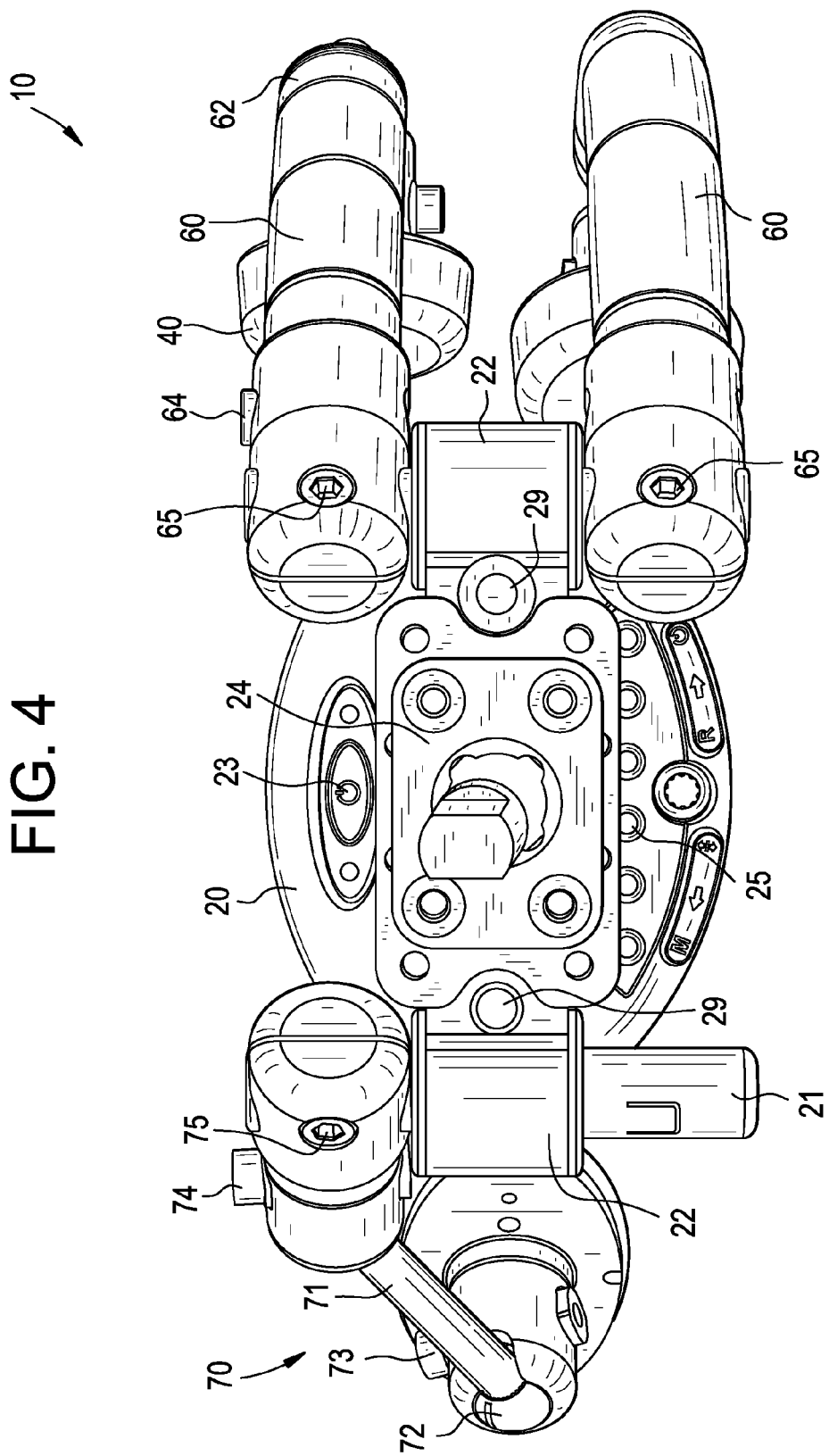
FIG. 4 is a diagram that illustrates a rear view of an exemplary head array system in accordance with an embodiment of the present invention.

FIG. 4 is a diagram that illustrates a rear view of an exemplary head array system 10 in accordance with an embodiment of the present invention. Referring to FIG. 4, there is shown a head array 10 comprising head array body 20, lateral sensors 40 and mode switch 50. Lateral arms 60, 70 couple sensors 40, 50 to head array body 20 at shafts 21. Telescoping lateral arm 60 may comprise a telescoping extension 61, securing mechanisms 62-65 and/or rotational mechanisms 66, for example. Swiveling lateral arm 70 may comprise a rod 71, securing mechanisms 73-75 and/or rotational mechanisms 72, for example.

Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example. Head array shafts 21 are attached to head array body 20 by shaft attachments 22. Each head array shaft 21 may be capable of receiving at least two lateral arms 60, 70. In various embodiments, shaft attachments 22 may attach to each head array shaft 21 such that each shaft 21 comprises an upper portion and a lower portion. Each of the upper and lower portions of each head array shaft 21 may be capable of receiving one or more lateral arms 60, 70. Lateral arms 60, 70 may be detachably coupled to shafts 21 such that lateral arms 60, 70 may be removed for cleaning, replacement, and/or reconfiguration of lateral arm 60, 70 placement, among other things, by removing or unlocking, for example, securing mechanism 65, 75. For example, a clinician, technician or caregiver may switch positions of sensor 40 and mode switch 50 by removing each of the lateral arms 60, 70 and reattaching the lateral arms 60, 70 at exchanged positions on head array shafts 21. Lateral arms 60, 70 may be fixably secured at a selected position on shafts 21 by tightening or locking, for example, securing mechanism 65, 75.

In various embodiments, enable/disable mechanism 23 may provide an indication to a microprocessor (not shown) housed in head array body 20 indicating whether the microprocessor should generate command signals in response to received activation signals from sensors 30, 40, 50. For example, if a disable mode for head array 10 is selected by a user or caregiver using the enable/disable mechanism 23, activation of sensors 30, 40, 50 would not result in commands being sent to power wheelchair and/or accessory components from head array 10. If an enable mode for head array 10 is selected by a user or caregiver using the enable/disable mechanism 23, activation of sensors 30, 40, 50 causes the microprocessor to generate corresponding command signals that are sent to power wheelchair and/or accessory components via an output interface (not shown) on head array body 20. Output interface may be a nine-pin sub-D connector, for example, or any other suitable output interface. Enable/disable mechanism 23 may be a button, switch or any other suitable enable/disable mechanism, for example.

In certain embodiments, enable/disable mechanism 23 may turn the power on (enable) and off (disable). For example, if a disable mode for head array 10 is selected by a user or caregiver using the enable/disable mechanism 23, sensors 30, 40, 50 may not be activated. If an enable mode for head array 10 is selected by a user or caregiver using the enable/disable mechanism 23, activation of sensors 30, 40, 50 causes the microprocessor to generate corresponding command signals that are sent to power wheelchair and/or accessory components via an output interface (not shown) on head array body 20. Output interface may be a nine-pin sub-D connector, for example, or any other suitable output interface. Enable/disable mechanism 23 may be a button, switch or any other suitable enable/disable mechanism, for example.

Certain embodiments provide a mounting plate 24 attached to head array body 20 for securing a wheelchair mount 28 that couples the head array 10 to a wheelchair. Wheelchair mount 28 may be any suitable mount capable of holding head array 10 in a fixed position around a user's head. Mounting plate 24 may be any suitable mounting plate capable of attaching to wheelchair mount 28. In certain embodiments, head array body 20 may be compatible with different mounting plate types. In various embodiments, the mounting plate 24 type used may correspond to the wheelchair mount 28 used. In certain embodiments, mounting plate 24 and wheelchair mount 28 may be integrated into a single component.

In various embodiments, head array body 20 comprises input jacks 25 operable to receive cable plugs from sensors 30, 40, 50, and the like. As noted above, existing head array devices are bulky and have disorganized cable management with multiple cable connections at different points on or around the power wheelchair. For example, cables can be untidily attached to an outer surface of the lateral arms. As another example, cables from different switches or sensors of existing head array devices may be routed to separate control boxes located at various locations on or around the power wheelchair. Certain embodiments provide cables neatly routed in channels or grooves 67 of lateral arm 60, 70 and/or lateral arm telescoping extension 61 to a central collection of input jacks 25 at head array body 20. The cable management between sensors 30, 40, 50 and input jacks 25 provides a clean finish. A clinician, technician or caregiver may set-up and/or change the configuration of the head array 10 based on the selection of which cable plug from each sensor 30, 40, 50 is plugged into each one of the input jacks 25. For example, if a cable from occipital pad sensor 30 plugged into a first input jack 25 is instead plugged into a fourth input jack 25, the microprocessor may generate a different command signal in response to receiving an activation signal from occipital pad sensor 30.

In certain embodiments, ferrite beads, or any other suitable electromagnetic suppression mechanism, may be used on cables at or near sensors 30, 40, 50 to allow head array 10 to comply with electromagnetic compatibility (EMC), electromagnetic interference (EMI), and electrostatic discharge (ESD) standards.

Certain embodiments provide adjustability of a front portion of head array body 20 relative to a rear portion of head array body 20 such that a position of an occipital pad may be adjusted. For example, head array body 20 may comprise a ball swivel joint mount 27 including a ball swivel joint 26 at a central portion of head array body 20 allowing movement of the front portion of head array body 20 attached to the occipital pad. As such, sensor 30 may be angled up, down, left or right by rotating the front portion of head array body 20 at ball swivel joint 26 or any other suitable rotational mechanism when a securing mechanism (not shown) is unlocked, loosened, or the like. Once the front portion of head array body 20 is rotated such that sensor 30 is at a desired position, the securing mechanism may be tightened, locked or the like, such that the front portion of head array body 20 is fixably secured at the selected position. The securing mechanism may be a clamp, bolt or any other suitable securing mechanism. In various embodiments, the securing mechanism may be a toolless securing mechanism. Further, the rotational mechanism 26, 27 may be any suitable rotational mechanism, for example.

In certain embodiments, head array body 20 comprises a swivel release mechanism 29 for allowing lateral arms 60, 70 to swing away from a user's head such that a caregiver can approach the user's head, for example. Swing release mechanism 29 may include an index for allowing the lateral arms 60, 70 to snap back in the original position such that manual repositioning of lateral arms 60, 70 is not required. In various embodiments, multiple swing release mechanisms 29 may be provided, each of the swing release mechanisms 29 corresponding to a shaft 21 and/or lateral arm 60, 70. In embodiments where a swing release mechanism 29 corresponds to a shaft 21 and more than one lateral arm 60, 70 is coupled to the shaft 21, activation of the swing release mechanism 29 may allow the lateral arms 60, 70 to swing away from a user's head in unison, for example.

The head array 10 illustrated in FIG. 4 shares various characteristics with the head array 10 illustrated in FIGS. 1-3 as described above.

Figure 5:
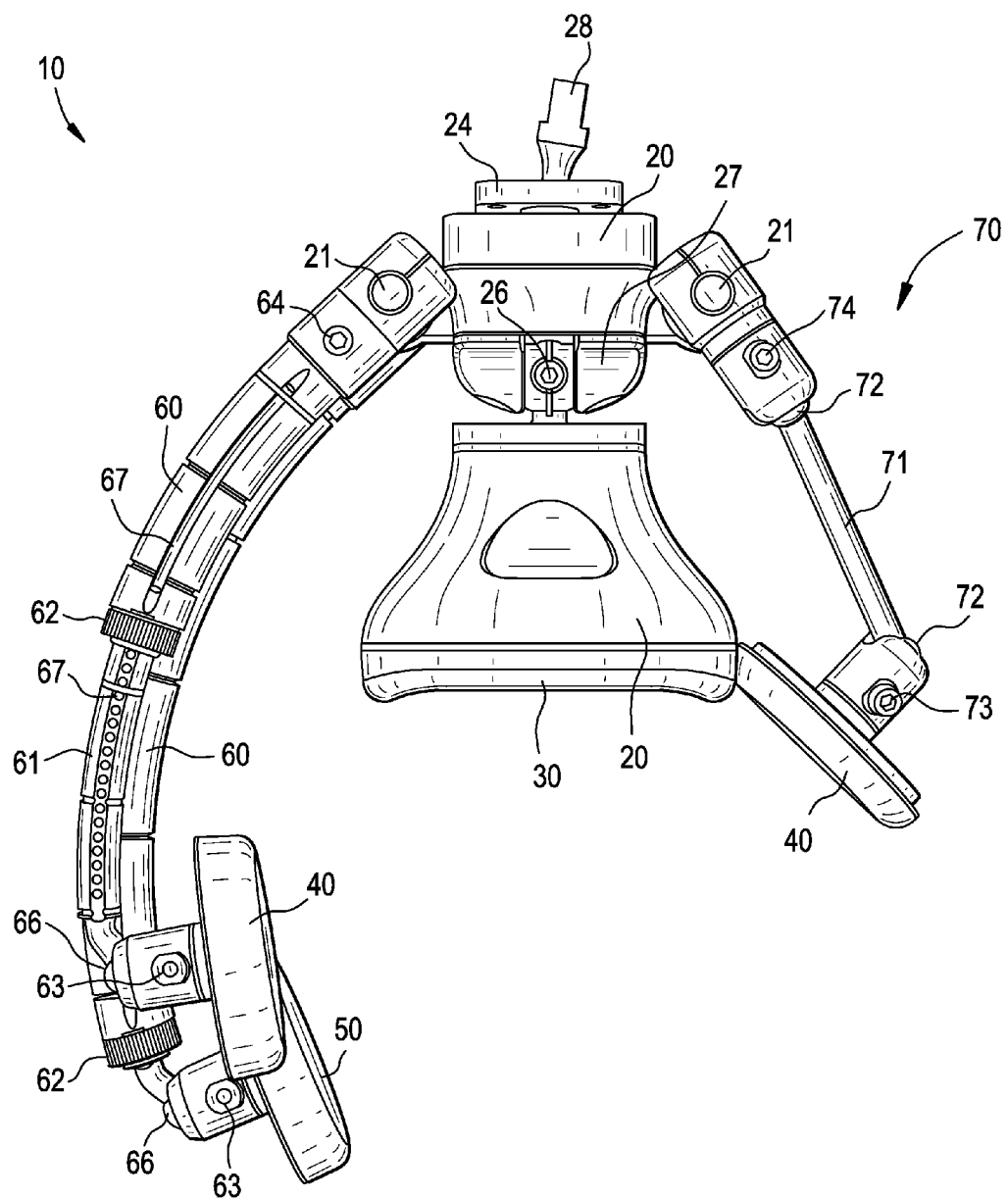
FIG. 5 is a diagram that illustrates a top view of an exemplary head array system in accordance with an embodiment of the present invention.

FIG. 5 is a diagram that illustrates a top view of an exemplary head array system 10 in accordance with an embodiment of the present invention. Referring to FIG. 5, there is shown a head array 10 comprising head array body 20, occipital pad sensor 30, lateral sensors 40 and mode switch 50. Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example. Occipital pad sensor 30 is attached to head array body 20. Lateral arms 60, 70 couple sensors 40, 50 to head array body 20 at shafts 21. Telescoping lateral arm 60 may comprise a telescoping extension 61, securing mechanisms 62-65 and/or rotational mechanisms 66, for example. Swiveling lateral arm 70 may comprise a rod 71, securing mechanisms 73-75 and/or rotational mechanisms 72, for example. The head array 10 illustrated in FIG. 5 shares various characteristics with the head array 10 illustrated in FIGS. 1-4 as described above.

Figure 6:
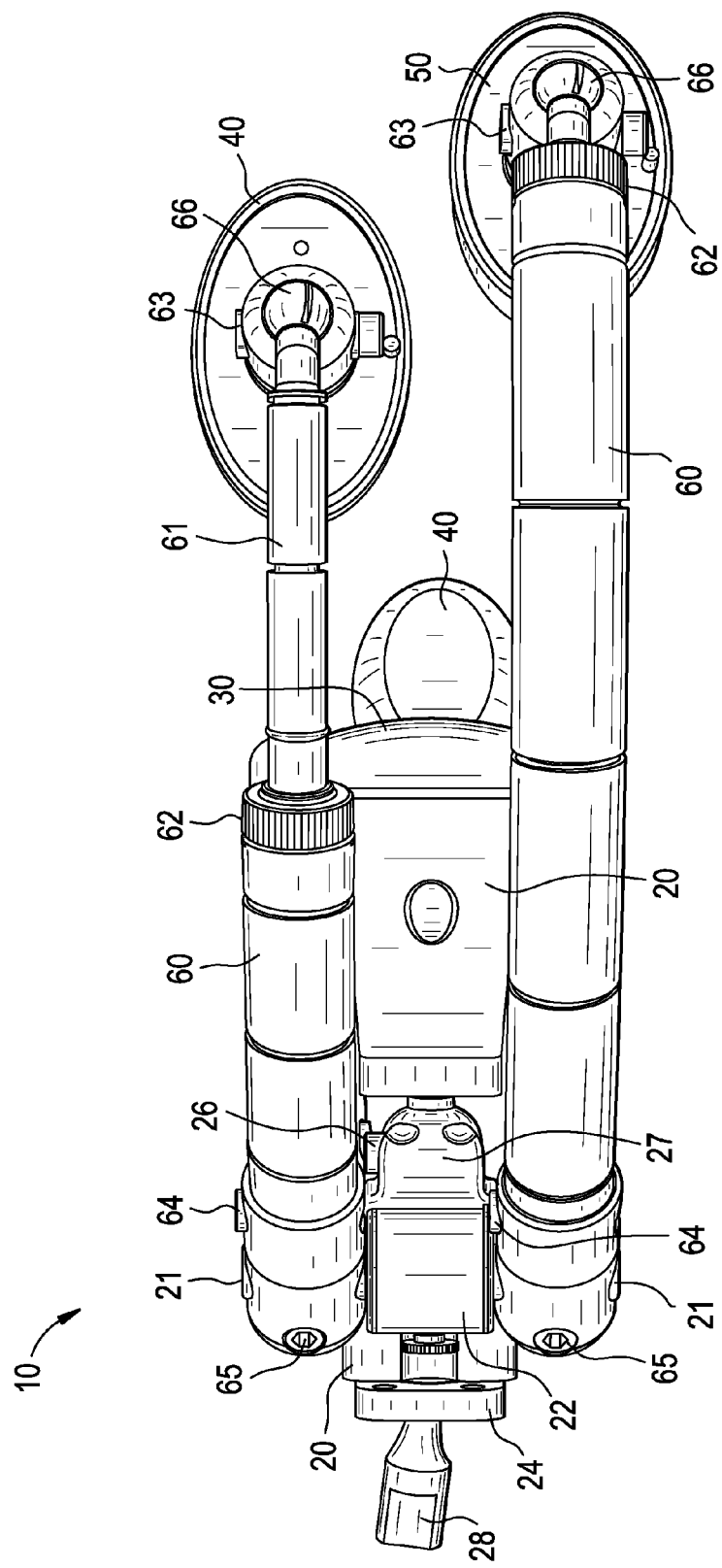
FIG. 6 is a diagram that illustrates a side view of an exemplary head array system in accordance with an embodiment of the present invention.

FIG. 6 is a diagram that illustrates a side view of an exemplary head array system 10 in accordance with an embodiment of the present invention. Referring to FIG. 6, there is shown a head array 10 comprising head array body 20, occipital pad sensor 30, lateral sensors 40 and mode switch 50. Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example. Occipital pad sensor 30 is attached to head array body 20. Lateral arms 60, 70 couple sensors 40, 50 to head array body 20 at shafts 21. Telescoping lateral arm 60 may comprise a telescoping extension 61, securing mechanisms 62-65 and/or rotational mechanisms 66, for example. The head array 10 illustrated in FIG. 6 shares various characteristics with the head array 10 illustrated in FIGS. 1-5 as described above.

Figure 7:
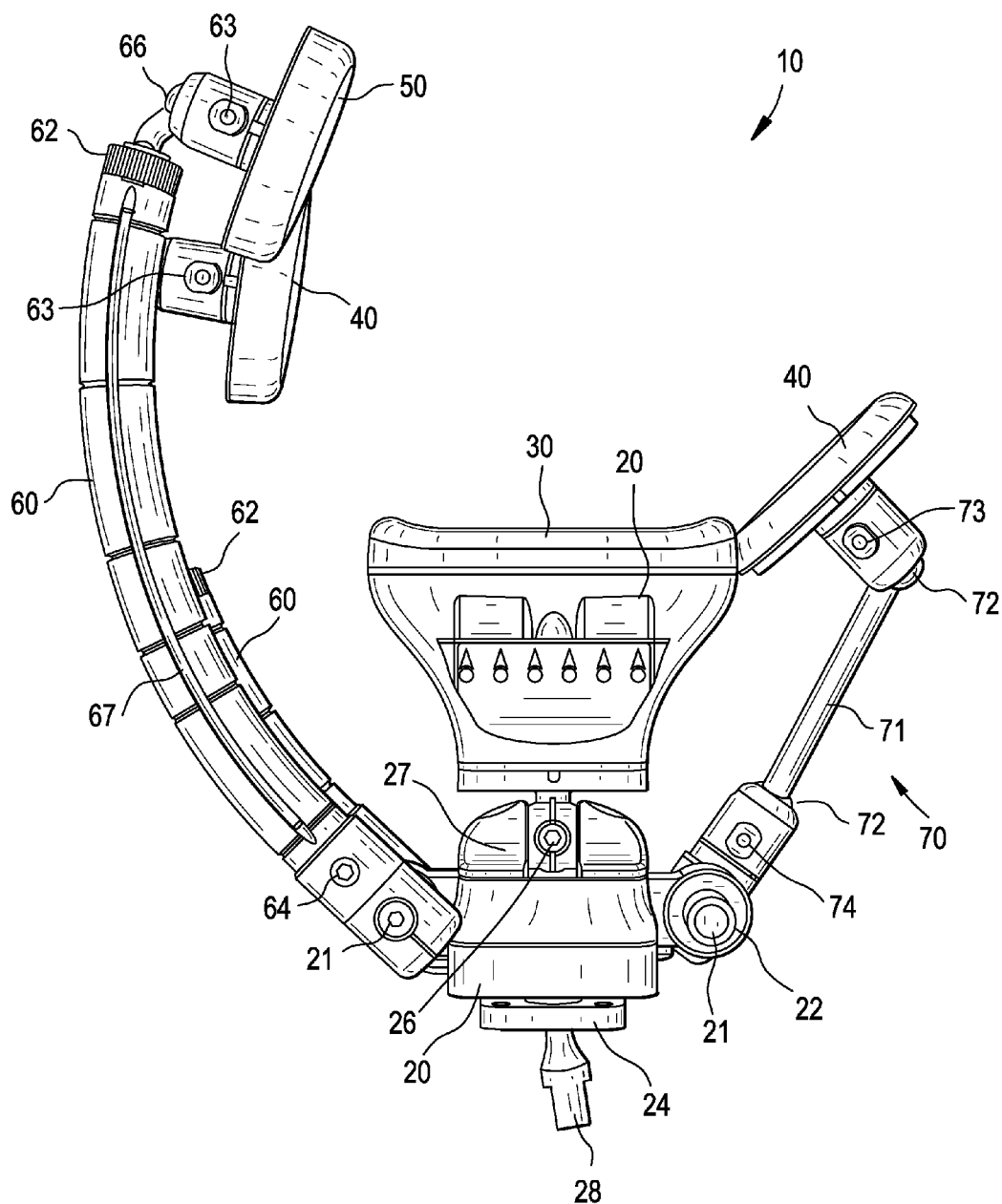
FIG. 7 is a diagram that illustrates a bottom view of an exemplary head array system in accordance with an embodiment of the present invention.

FIG. 7 is a diagram that illustrates a bottom view of an exemplary head array system 10 in accordance with an embodiment of the present invention. Referring to FIG. 7, there is shown a head array 10 comprising head array body 20, occipital pad sensor 30, lateral sensors 40 and mode switch 50. Head array body 20 comprises head array shafts 21, shaft attachments 22, enable/disable mechanism 23, mounting plate 24, input jacks 25, output interface (not shown), ball swivel joint 26, ball swivel joint mount 27, wheelchair mount 28 and/or swivel release mechanisms 29, for example. Occipital pad sensor 30 is attached to head array body 20. Lateral arms 60, 70 couple sensors 40, 50 to head array body 20 at shafts 21. Telescoping lateral arm 60 may comprise a telescoping extension 61, securing mechanisms 62-65 and/or rotational mechanisms 66, for example. Swiveling lateral arm 70 may comprise a rod 71, securing mechanisms 73-75 and/or rotational mechanisms 72, for example. The head array 10 illustrated in FIG. 7 shares various characteristics with the head array 10 illustrated in FIGS. 1-6 as described above.

Certain embodiments provide a head array system 10 for a power wheelchair, comprising a head array body 20 and one or more lateral arms 60, 70. The head array body 20 comprises shafts 21. Each of the shafts 21 comprises lateral arm receiving sections. The one or more lateral arms 60, 70 are detachably coupled to one of the lateral arm receiving sections of one of the shafts 21.

In various embodiments, the one or more lateral arms 60, 70 comprise a plurality of lateral arms 60, 70. Each of the plurality of lateral arms 60, 70 is detachably coupled to one of the lateral arm receiving sections of one of the shafts 21. In an embodiment, the head array system 10 is reconfigurable by removing at least one of the plurality of lateral arms 60, 70 from the one of the lateral arm receiving sections and reattaching the removed at least one of the plurality of lateral arms 60, 70 to another of the lateral arm receiving sections of one of the shafts 21.

In certain embodiments, the head array system 10 comprises one or more of a switch 40, 50 and a sensor 40, 50 coupled to the head array body 20 via the one or more lateral arms 60, 70. In an embodiment, the head array body 20 comprises input jacks 25. Each of the input jacks 25 is operable to receive a cable plug from the one or more of the switch 40, 50 and the sensor 40, 50. In an embodiment, the head array body 20 comprises a microprocessor and an enable/disable mechanism 23. The enable/disable mechanism 23 instructs the microprocessor to generate command signals in response to received activation signals from the one or more of the switch 40, 50 and the sensor 40, 50 if the enable/disable mechanism 23 is in a selected enable mode. The enable/disable mechanism 23 instructs the microprocessor to disregard received activation signals from the one or more of the switch 40, 50 and the sensor 40, 50 if the enable/disable mechanism 23 is in a selected disable mode.

In various embodiments, the head array body 20 comprises shaft attachments 22. Each of the shaft attachments 22 attaches to one of the shafts 21 such that each of the shafts 21 comprises an upper portion and a lower portion. Each of the upper portion and the lower portion of each of the shafts 21 is operable to receive one of the plurality of lateral arms 60, 70. In an embodiment, the head array body 20 comprises a ball swivel joint mount 27 comprising a ball swivel joint 26 at a central portion of the head array body 20 allowing movement of a front portion of the head array body 20 relative to a rear portion of the head array body 20.

In certain embodiments, the head array body 20 comprises a swivel release mechanism 29 operable to release the one or more lateral arms 60, 70 from an original position such that the one or more lateral arms 60, 70 are rotated away from the head array body 20. The swing release mechanism 29 comprises an index such that the one or more lateral arms snap back in the original position when the one or more lateral arms is rotated toward the head array body 20. In an embodiment, the head array system 10 complies with electromagnetic compatibility (EMC), electromagnetic interference (EMI), and electrostatic discharge (ESD) standards.

Certain embodiments provide a head array system 10 for a power wheelchair, comprising a head array body 20, one or more of a sensor 40, 50 and a switch 40, 50, and one or more lateral arms 60 operable to couple the one or more of the sensor 40, 50 and the switch 40, 50 to the head array body 20. The one or more lateral arms 60 comprise a hollow, curved lateral arm tube 60 attached to the head array body 20, a curved telescoping extension 61 attached to the one or more of the sensor 40, 50 and the switch 40, 50, and a first securing mechanism 62. The telescoping extension 61 is slidable from a selectable non-extended position, where the telescoping extension 61 is substantially housed within the lateral tube 60, to selectable extension positions at least partially outside of the lateral arm tube 60. The first securing mechanism 62 is operable to lock the telescoping extension 61 into one or more of the selectable non-extended positions and the selectable extension positions.

In various embodiments, the first securing mechanism 62 is a toolless locking ring. In an embodiment, the head array system 10 comprises a second securing mechanism 63 operable to secure the one or more of the sensor 40, 50 and the switch 40, 50 to the telescoping extension 61 at a rotational mechanism 66. In an embodiment, the second securing mechanism 63 in an unlocked position allows for rotation of the one or more of the sensor 40, 50 and the switch 40, 50 around the rotational mechanism 66 such that a presentation angle of the one or more of the sensor 40, 50 and the switch 40, 50 is selectable, and/or allows for removal of the one or more of the sensor 40, 50 and the switch 40, 50.

In certain embodiments, the second securing mechanism 63 in a locked position fixably secures the one or more of the sensor 40, 50 and the switch 40, 50 to the telescoping extension 61 at the selected presentation angle. In an embodiment, the rotational mechanism 66 is a ball joint.

In various embodiments, the one or more lateral arms 60 comprise a second securing mechanism 64 operable to secure the one or more lateral arms 60 at a selected rotation in a vertical plane. The second securing mechanism 64 in an unlocked position allows for rotation of the one or more lateral arms 60 to a selected position in the vertical plane. The second securing mechanism 64 in a locked position fixably secures the one or more lateral arms at the selected position in the vertical plane.

In certain embodiments, the head array body 20 comprises one or more shafts 21 and the one or more lateral arms 60 comprise a second securing mechanism 65 operable to secure the one or more lateral arms 60 to the head array body 20. In an embodiment, the second securing mechanism 65 in an unlocked position allows for rotation of the one or more lateral arms in a horizontal plane around the one or more shafts such that a distance between the one or more of the sensor 40, 50 and the switch 40, 50 and a user's head is selectable, and/or allows for removal of the one or more lateral arms 60. In an embodiment, the second securing mechanism 65 in a locked position fixably secures the one or more lateral arms 60 to the one or more shafts 21 of the head array body 20 at the selected distance.

Certain embodiments provide a head array system 10 for a power wheelchair, comprising a head array body 20 and an occipital pad. The head array body 20 comprises a microprocessor configured to generate command signals in response to sensor activation signals. The occipital pad is attached to the head array body 20 and comprises a plurality of sensors 30. Each of the plurality of sensors 30 is configured to transmit an activation signal to the microprocessor in response to sensor activation. The microprocessor generates a command signal if the microprocessor receives the activation signal from all of the plurality of sensors 30 in the occipital pad, and disregards the activation signal if the microprocessor receives the activation signal from less than all of the plurality of sensors 30 in the occipital pad.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A head array system for a power wheelchair, comprising:
   a head array body comprising shafts, wherein each of the shafts comprises lateral arm receiving sections;
   at least one lateral arm detachably coupled to one of the lateral arm receiving sections of one of the shafts; and
   at least one of a switch and a sensor coupled to the head array body via the at least one lateral arm,
   wherein the head array body comprises a microprocessor and an enable/disable mechanism, wherein the enable/disable mechanism instructs the microprocessor to:
   generate command signals in response to received activation signals from the at least one of the switch and the sensor if the enable/disable mechanism is in a selected enable mode, and
   disregard received activation signals from the at least one of the switch and the sensor if the enable/disable mechanism is in a selected disable mode.

2. The head array system according to claim 1, wherein the at least one lateral arm comprises a plurality of lateral arms, each of the plurality of lateral arms detachably coupled to one of the lateral arm receiving sections of one of the shafts.

3. The head array system according to claim 2, wherein the head array system is reconfigurable by removing at least one of the plurality of lateral arms from the one of the lateral arm receiving sections and reattaching the removed at least one of the plurality of lateral arms to another of the lateral arm receiving sections of one of the shafts.

4. The head array system according to claim 2, wherein the head array body comprises shaft attachments, wherein each of the shaft attachments attaches to one of the shafts such that each of the shafts comprises an upper portion and a lower portion, and wherein each of the upper portion and the lower portion of each of the shafts is operable to receive one of the plurality of lateral arms.

5. The head array system according to claim 1, wherein the head array body comprises input jacks, wherein the input jacks are each operable to receive a cable plug from the at least one of the switch and the sensor.

6. The head array system according to claim 1, wherein the head array body comprises a ball swivel joint mount comprising a ball swivel joint at a central portion of the head array body allowing movement of a front portion of the head array body relative to a rear portion of the head array body.

7. The head array system according to claim 1, wherein the head array body comprises a swivel release mechanism operable to release the at least one lateral arm from an original position such that the at least one lateral arm is rotated away from the head array body, and wherein the swivel release mechanism is indexed such that the at least one lateral arm snaps back in the original position when the at least one lateral arm is rotated toward the head array body.

8. The head array system according to claim 1, wherein the head array system complies with EN 12184:2009 and ISO 7176-21:2003.

9. The head array system according to claim 1, wherein the at least one lateral arm is directly connected to the one of the lateral arm receiving sections of the one of the shafts.

10. The head array system according to claim 1, wherein the shafts comprise a longitudinal axis substantially perpendicular to a detachably coupled at least one lateral arm.

11. The head array system according to claim 1, wherein the shafts are parallel to each other in an upright position.

12. A head array system for a power wheelchair, comprising:
   a head array body;
   at least one of a sensor and a switch; and
   at least one lateral arm operable to couple the at least one of the sensor and the switch to the head array body, wherein the at least one lateral arm comprises:
      a hollow, curved lateral arm tube attached to the head array body,
      a curved telescoping extension attached to the at least one of the sensor and the switch, wherein the telescoping extension is slidable from a selectable non-extended position, where the telescoping extension is substantially housed within the lateral tube, to selectable extension positions at least partially outside of the lateral arm tube, and
      a first securing mechanism operable to lock the telescoping extension into at least one of the selectable non-extended position and the selectable extension positions.

13. The head array according to claim 12, wherein the first securing mechanism is a toolless locking ring.

14. The head array according to claim 12, comprising a second securing mechanism operable to secure the at least one of the sensor and the switch to the telescoping extension at a rotational mechanism.

15. The head array according to claim 14, wherein the second securing mechanism in an unlocked position allows for at least one of:
   rotation of the at least one of the sensor and the switch around the rotational mechanism such that a presentation angle of the at least one of the sensor and the switch is selectable, and
   removal of the at least one of the sensor and the switch.

16. The head array according to claim 15, wherein the second securing mechanism in a locked position fixably secures the at least one of the sensor and the switch to the telescoping extension at the selected presentation angle.

17. The head array according to claim 15, wherein the rotational mechanism is a ball joint.

18. The head array according to claim 12, wherein the at least one lateral arm comprises a second securing mechanism operable to secure the at least one lateral arm at a selected rotation in a vertical plane, wherein the second securing mechanism in an unlocked position allows for rotation of the at least one lateral arm to a selected position in the vertical plane, and wherein the second securing mechanism in a locked position fixably secures the at least one lateral arm at the selected position in the vertical plane.

19. The head array according to claim 12, wherein the head array body comprises at least one shaft and the at least one lateral arm comprises a second securing mechanism operable to secure the at least one lateral arm to the head array body.

20. The head array according to claim 19, wherein the second securing mechanism in an unlocked position allows for at least one of:
   rotation of the at least one lateral arm in a horizontal plane around the at least one shaft such that a distance between the at least one of the sensor and the switch and a user's head is selectable, and
   removal of the at least one lateral arm.

21. The head array according to claim 20, wherein the second securing mechanism in a locked position fixably secures the at least one lateral arm to the at least one shaft of the head array body at the selected distance.

22. A head array system for a power wheelchair, comprising:
   a head array body comprising a microprocessor configured to generate command signals in response to sensor activation signals; and
   a plurality of sensors in an occipital pad attached to the head array body, each of the plurality of sensors configured to transmit an activation signal to the microprocessor in response to sensor activation,
   wherein the microprocessor:
      generates a command signal if the microprocessor receives the activation signal from all of the plurality of sensors in the occipital pad, and
      disregards the activation signal if the microprocessor receives the activation signal from less than all of the plurality of sensors in the occipital pad.

* * * * *